(12) United States Patent
Keller et al.

(10) Patent No.: US 9,254,464 B2
(45) Date of Patent: Feb. 9, 2016

(54) FILTER MODULE

(75) Inventors: Torsten Keller, Hermeskeil (DE); Franz Kugelmann, Sankt Wendel (DE); Wolfgang Wehmeyer, Tuebingen (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 9 days.

(21) Appl. No.: 13/551,222

(22) Filed: Jul. 17, 2012

(65) Prior Publication Data

US 2013/0020250 A1 Jan. 24, 2013

Related U.S. Application Data

(60) Provisional application No. 61/457,957, filed on Jul. 18, 2011.

(30) Foreign Application Priority Data

Jul. 18, 2011 (DE) .......................... 10 2011 107 980

(51) Int. Cl.
*B01D 63/04* (2006.01)
*B01D 27/14* (2006.01)
(Continued)

(52) U.S. Cl.
CPC ................ *B01D 63/04* (2013.01); *B01D 61/58* (2013.01); *A61M 1/3413* (2013.01);
(Continued)

(58) Field of Classification Search
CPC .. B01D 24/004; B01D 24/005; B01D 24/008; B01D 24/002; B01D 27/144; B01D 27/148; B01D 29/0054; B01D 29/0056; B01D 29/0059; B01D 29/54; B01D 29/58; B01D 33/39; B01D 33/42; B01D 46/0021; B01D 46/0024; B01D 2313/04; B01D 2313/21; B01D 2313/58; B01D 2319/025; B01D 27/114; B01D 29/59; B01D 63/005–63/068; B01D 69/08–69/088; C02F 2201/003

USPC ............... 210/321.72, 321.6, 321.64, 321.79, 210/321.8, 321.81, 321.88, 321.89, 321.9, 210/456, 645, 646; 604/6.09, 6.04, 6.1, 604/6.11, 4.01, 5.01, 5.02, 5.03, 5.04
See application file for complete search history.

(56) References Cited

U.S. PATENT DOCUMENTS 4,368,124 A * 1/1983 Brumfield ................ 210/321.79
4,861,485 A 8/1989 Fecondini
(Continued)

FOREIGN PATENT DOCUMENTS

DE 82 15 355.8 9/1982
DE 33 26 704 1/1985
(Continued)

OTHER PUBLICATIONS

English language machine translation of DE 3326704, pp. 1-3.*

*Primary Examiner* — David C Mellon
*Assistant Examiner* — Pranav Patel
(74) *Attorney, Agent, or Firm* — Jacobson Holman, PLLC.

(57) ABSTRACT

A filter module includes a first filter stage and a second filter stage which are substantially concentrically arranged. The first filter stage and the second filter stage each include a plurality of hollow fiber membranes having a first fiber end and a second fiber end, which are embedded in a respective casting compound. The first filter stage is a filter stage for the filtration of a first medical fluid, and the second filter stage is a filter stage for the filtration of a second medical fluid. The first filter stage has unilaterally closed fiber ends, and is surrounded by a boundary element which separates the first filter stage and the second filter stage from one another. The boundary element has at least one opening which provides fluid communication between the first filter stage and the second filter stage.

16 Claims, 4 Drawing Sheets

(51) Int. Cl.
  B01D 69/08 (2006.01)
  B01D 61/58 (2006.01)
  A61M 1/34 (2006.01)
  B01D 61/14 (2006.01)
  B01D 61/24 (2006.01)

(52) U.S. Cl.
  CPC ............ *B01D 61/145* (2013.01); *B01D 61/243* (2013.01); *B01D 2313/04* (2013.01); *B01D 2313/21* (2013.01); *B01D 2313/58* (2013.01); *B01D 2319/025* (2013.01)

(56) References Cited

U.S. PATENT DOCUMENTS

| | | | | |
|---|---|---|---|---|
| 5,183,566 A | * | 2/1993 | Darnell et al. | 210/321.8 |
| 5,817,279 A | * | 10/1998 | Eilers et al. | 422/46 |
| 5,882,516 A | | 3/1999 | Gross et al. | |
| 5,942,112 A | | 8/1999 | Ishak | |
| 6,149,817 A | * | 11/2000 | Peterson et al. | 210/644 |
| 6,719,907 B2 | * | 4/2004 | Collins et al. | 210/646 |
| 2006/0081524 A1 | * | 4/2006 | Sengupta et al. | 210/321.88 |

FOREIGN PATENT DOCUMENTS

| | | |
|---|---|---|
| DE | 39 01 446 | 8/1989 |
| EP | 0 791 368 | 8/1997 |
| JP | 06-006156 | 2/1994 |

* cited by examiner

FILTER MODULE

CROSS-REFERENCE TO RELATED APPLICATIONS

This application claims the benefit of U.S. provisional application No. 61/457,957, filed Jul. 18, 2011, and priority of German number 10 2011 107 980.0 filed Jul. 18, 2011, hereby incorporated by reference.

BACKGROUND OF THE INVENTION

1. Field of Invention

The present invention relates to a filter module and to a method of manufacturing a hollow fiber membrane bundle having at least two concentrically arranged filter stages. The invention in particular relates to filter modules for hemodialysis, in particular to filter modules which integrally contain a plurality of filtration stages.

2. Description of the Prior Art

A plurality of filters are required for a number of therapeutic processes of extracorporeal blood purification. In these processes, blood is as a rule filtered or dialyzed at hollow fiber membranes of a filter module for purifying toxic metabolites. High demands are made in this respect on the fluids used for substitution or for dialysis to be able to be used in the therapeutic processes. Such fluids are provided in pouches licensed under drug law or are manufactured online by the extracorporeal blood treatment machines. To be able to ensure the microbiological purity in the online processes, these fluids have to run through one or two filtration stages before they may be used as replacement fluids in dialysis or as substitution fluids in blood filtration processes.

There have previously been endeavors to design the fluid circuits of extracorporeal blood treatment circuits more compact and to integrate them for disposable articles. Cassette systems for extracorporeal blood treatment have in particular been developed for which a plurality of functions for blood treatment and fluid treatment are integrated.

Developments have equally been promoted in the field of blood filters using hollow fiber membranes in which a plurality of filter stages have been integrated in a filter module.

EP 0 791 368 A2 shows a two-stage filter module for hemodiafiltration. In a first stage, inflowing substitution fluid penetrates into the interior of the hollow fiber membrane, is filtered in so doing and is mixed with blood in a blood chamber at the head end of the filter module. In a second stage, the diluted blood runs through the interior of the hollow fiber membranes and is dialyzed and filtrated in so doing.

DE 39 01 446 A1 describes a two-stage filter having a first stage in which dialysis fluid is directed into the interior of the hollow fiber membranes, passes through the membrane and is filtered in so doing. The filtrate of the first stage is directly directed into the second stage and there flows through the outer space of the hollow fiber membrane bundle as dialysis fluid.

DE 33 26 704 A1 shows a two-stage filter module in which the hollow fiber membrane bundles are concentrically arranged. Blood is filtered in an inner first filtration stage. In the second, surrounding filtration stage, blood is treated in substance exchange with dialysis fluid.

SUMMARY OF THE INVENTION

It is therefore the object of the present invention to further develop in an advantageous manner a filter module and a method of manufacturing a hollow fiber membrane bundle having two concentrically arranged filter stages, in particular such that the setup of a medical fluid circuit can be simplified using the filter module.

This object is achieved in accordance with the invention by a filter module having at least one first filter stage and at least one second filter stage is manufactured comprising and/or consisting of hollow fiber membranes which are arranged substantially concentrically, wherein the fiber ends of the hollow fiber membranes are embedded at least partly and/or at least unilaterally in a casting compound, wherein the first filter stage is a filter stage for filtration of a first medical fluid and the second filter stage is a filter stage for filtration of a second medical fluid, wherein the first filter stage has closed fiber ends at one side, wherein a bounding means surrounding the first filter module is provided which separates the first filter stage and the second filter stage at least partly from one another and has at least one opening which establishes a filter communication between a first filter stage and a second filter stage.

The advantage thereby results that an integrated arrangement of an ultrafilter and a blood filter can be achieved in a single filter housing of a filter module. The advantage hereby in particular results that a cost reduction can be achieved by lower material use since now two to three filters can be integrated for a single filter or the function of two to three filters can be achieved by a single filter module.

It is furthermore possible to use an extruded housing, whereby a cost reduction can be achieved in comparison with injection molding manufacturing processes. It is furthermore possible by a simplified setup which results from the filter module in accordance with the invention to simplify the setup of a blood treatment apparatus such as a dialysis machine overall, for instance such that fewer valves, hoses or less electronics or software is/are required or is/are required in less complex form. An advantage furthermore results in that the filter module can be designed completely as a disposable article, that is as a so-called disposable, whereby overall a higher security can be achieved by individual product tests in production before each use at lower costs. It is in particular no longer necessary to perform a reuse of sterile filters on the dialysis side of a blood treatment apparatus such as a dialysis machine.

It is furthermore possible to achieve a reduction of test times during dialysis, for which purpose filter integrity tests have previously had to be used since the sterile filters on the dialysis side are reused. A higher dialysis dosage for the patient can hereby be achieved. In addition, it is possible to achieve a higher dialysis dosage with an unchanged area flowed through by blood since a better dialysate distribution can be achieved by means of the filter module in accordance with the invention.

Provision can be made that the first medical fluid is a dialyzing liquid and/or a substitution fluid and/or that the second medical fluid is blood and/or that the first filter stage is surrounded by the second filter stage. Provision can be made in this respect that the first filter stage is designed in the form of a substantially cylindrical hollow fiber bundle, whereas the second filter stage is designed in the form of a hollow cylindrical hollow fiber bundle in which the first filter stage is arranged.

Provision is in particular made that the second filter stage in each case has unclosed fiber ends at both sides.

It is furthermore possible that the boundary means has and/or forms a boundary wall and that the opening in the boundary means is arranged in the boundary wall in the region adjacent to the casting compound and/or that the boundary means has at least one venting opening. Openings in the boundary wall in the region adjacent to the casting compound can be arranged peripherally in the boundary wall, e.g. by perforating and/or piercing this section of the boundary wall. A uniform transition of the filtrate into the second filter stage and an optimized onflow of the fibers in the second filter stage thus takes place at the periphery of the first filter stage. A venting opening which is preferably designed with an opening smaller in comparison with the opening arranged in the boundary means is in particular sensible when the filter module is set slightly slanted, with the blood entry side being somewhat higher. The venting of the filter module is hereby facilitated. Since, however, a small quantity of dialysate can flow directly to the dialysate outlet during operation, whereby the performance might be negatively influenced, it is expedient to provide a comparatively small opening as a venting opening. It is generally also conceivable that a plurality of openings are provided in the boundary means, with the openings being arranged running around the periphery of the boundary means. It hereby becomes possible to achieve a particularly uniform distribution of the dialysate so that the second filter stage is flowed about by dialysate uniformly on its outer side.

It is possible that the boundary means is or comprises a film and/or a tube.

Provision can furthermore be made that the opening in the boundary means is formed from one or from a plurality of openings arranged peripherally at the boundary means, with the openings preferably being peripherally arranged slits, perforations, holes, labyrinth slits or the like.

Provision can furthermore be made that the filter module has a first end cap in which a connection to the first filter stage and a connection to the second filter stage is arranged, with the fiber ends of the first filter stage being unclosed on the side of the first end cap and with at least one sealing element being provided by means of which the unclosed fiber ends of the first filter stage can be and/or are sealed from the connection to the second filter stage and from the second filter stage.

It is furthermore possible that the filter module has a second end cap in which a connection to the second filter stage is arranged and/or that the fiber ends of the first filter stage are closed on the side of the second end cap.

Provision can moreover be made that the filter module has a housing in which the filter stages are arranged, with at least one connection to the first filter stage being arranged in the housing.

A connection can generally be an inflow to or an outflow to a filter stage since it is generally possible to operate the filter module in both the one and in the other fluid direction, that is to have a fluid flow through the filter stages both in the one direction and in the other direction.

Provision can furthermore be made that at least one passage element is provided concentrically and coaxially to the longitudinal axis of the filter module and/or to the filter stages, said passage element being connected to the second filter stage, and/or that at least one passage element is provided at the outer side of the filter module and is connected to the second filter stage.

It is furthermore conceivable that the filter module has at least one pump element and/or can be connected to at least one pump element, by means of which the first and/or second medical fluid can be pumped.

Provision can moreover be made that the pump element is a pump element integrated into the filter module and/or that the pump element is an impeller pump.

It is furthermore possible that a third filter stage is provided, with the first filter stage and the third filter stage being arranged with respect to one another such that the first medical fluid can be introduced from the first filter stage into the third filter stage via and/or through the hollow fiber membranes of the first and third filter stages.

It is furthermore conceivable that the first, second and third filter stages are arranged concentrically and coaxially, with the first filter stage surrounding the third filter stage and the second filter stage surrounding the first filter stage.

Provision can moreover be made that the filter module has a first end cap into which a connection to the first filter stage and a connection to the second filter stage is arranged, with the fiber ends of the first filter stage being unclosed on the side of the first end cap and with at least one sealing element being provided by means of which the unclosed fiber ends of the first filter stage can be and/or are sealed from the inflow to the first filter stage and from the second filter stage, with the fiber ends of the third filter stage being closed on the side of the first end cap, with a second end cap being provided in which a connection of the third filter stage is arranged and with the fiber ends of the third filter stage being unclosed on the side of the second end cap.

Provision can furthermore be made that at least one pump element can be and/or is connected to the connection to the third filter stage, with the pump element preferably being an integrated pump element and/or with the connection to the third filter stage being connectable and/or connected to the third filter stage using a connection to the second filter stage.

The present invention furthermore relates to a method of manufacturing a hollow fiber membrane bundle having two concentrically arranged filter stages. The method includes at least the following steps:

surrounding a first hollow fiber membrane bundle for a first filter stage in a film, tube film and/or a tube;
embedding the first filtration stage in hollow fibers of the second filtration stage;
molding the first and second filtration stage by a casting compound in a molding process;
cutting off an end region of the casting compound, including closed fiber ends, for exposing and laying open all fiber ends; and
closing a fiber end side of the first filtration stage by thermal influence and melting the fiber end side and the casting compound.

Processes for molding hollow fiber bundles are known in the prior art, e.g. for instance from JP 06-006156. The fiber ends first have to be closed so that no casting mold can penetrate into the fiber. This is already done by smelting processes with thermal effect on the fiber ends, e.g. by laser irradiation, heat mirrors or hot stamps. Subsequently, the casting takes place with a hardening castable compound, e.g. polyurethane materials, so that the fiber ends are closed except for some centimeters by the casting compound. Subsequently a cut takes place through the casting compound at the outer end of the fiber ends so that the closed fiber ends embedded in the casting compound are cut off. The fiber bundle cast at the end and now having open fiber ends remains.

To close the ends of a filtration stage in the manufacturing process again as in the present invention, a further step of closing the hollow fiber ends has to take place. A filtration stage can be closed by melting the casting compound having fiber ends by a repeated geometrically precise application of heat on a zone of the hollow fiber bundle including a plurality of filtration stages. The heat application can take place, for example, by laser, heat mirror or hot stamp.

Provision can in particular be made that the closing of the fiber end side takes place by means of laser and/or hot stamp.

It is furthermore conceivable that a third filtration stage is formed in the first filtration stage, with a first region being closed on a fiber end side and with a second region being closed on the other fiber end side, with hollow fibers being closed in the first region and these hollow fibers being surrounded by the second region on the other fiber end side and being at least partly unclosed.

It can hereby be achieved that the fluid, e.g. the dialysate, first enters into the first filter stage on the one fiber end side and cannot enter into the third filter stage due to the closed fiber ends. A transition of the fluid from the first filter stage into the third filter stage can thus advantageously only take place via the membranes of the hollow fiber membranes of the first and third filter stages. Since the hollow fiber ends of the first filter stage are closed on the other fiber end side and the hollow fiber ends of the third filter stage are unclosed, the fluid cannot pass unfiltered, but must rather flow through the membranes. The fluid, e.g. a medical fluid such as dialysate, is hereby securely filtered.

It is possible that a third filtration stage is formed in the first filtration stage, with a first region being closed on one fiber end side and a second region being closed on the other fiber end side, with hollow fibers being closed in the first region and these hollow fibers being surrounded and at least partly unclosed on the other fiber end side and that the first region is circular and the second region is annular, with the inner diameter of the second region preferably being selected to be smaller than the outer diameter of the first region. The outlet diameter of the fiber bundle of the third filter stage is hereby made smaller, for example, than the core diameter of the molded or closed bundle on the entry side of the third filter stage. It is thus advantageously ensured that dialysate is always filtered in two stages before it e.g. is infused into the extracorporeal blood circuit as postdilution and/or predilution. It can thereby in particular be achieved that individual fibers which are unexpectedly obliquely disposed in the total bundle by the production do not project from the third filter stage into the first filter stage. A two-stage filtration can thereby be ensured simply, reliably and advantageously.

Provision can furthermore be made that, in at least one further step, a filter module as described herein is manufactured from the hollow fiber membrane bundle.

The present invention furthermore relates to a disposable element that includes at least one filter module as described herein, and that is or includes a disposable cassette.

Provision can furthermore be made that the disposable is and/or comprises a disposable cassette.

The present invention furthermore relates to a blood treatment apparatus that has at least one filter module and/or a disposable element as described herein.

BRIEF DESCRIPTION OF THE DRAWINGS

Further details and advantages of the invention will now be explained in more detail with reference to an embodiment shown in the drawing.

There are shown

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
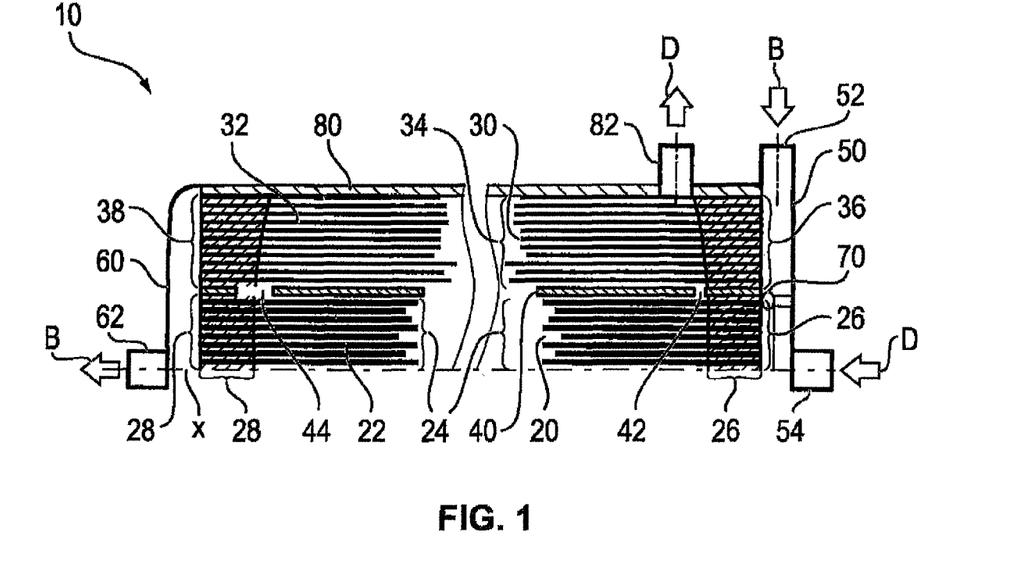
FIG. 1: a schematic representation of a filter module through a section along the central axis of symmetry of the concentric fiber bundle.

FIG. 1 shows a schematic representation of a single-stage integrated ultrafilter as a first filter stage 20 in a filter module 10, with only the upper half of the filter module 10 substantially radially symmetrical to the axis X being shown.

The core of the fiber bundle of the first filter stage 20 comprises the ultrafilter membranes 22. They can be identical to the blood filter membranes 32 of the second filter stage 30, but can also be adapted in membrane structure (high CUF for water; CUF=ultrafiltration coefficient) and dimensions (small inner diameter) to the object of the water filtration.

This fiber bundle 24 of the first filter stage 20 is surrounded by a boundary means 40 in the form of a tubular film or a tube which shows a housing having an outlet 44 at one side. The opening 44 can include a plurality of openings peripherally at the tube 40 so that a radially uniform transfer of the filtrate from the first filter stage 20 into the second filter stage 30 takes place. The dialysate enters at an end face through the connection 54 which is arranged in the end cap 50 and which is a dialysate inlet 54, through the unclosed hollow fiber membrane ends 26 into the lumen of the first filter stage 20 which is an ultrafilter stage and is discharged through the wall into the inner region of the fiber bundle 24 since the ends 28 of the hollow fibers 22 of the first filter stage 20 are completely closed on the side of the second end cap 60.

Figure 2:
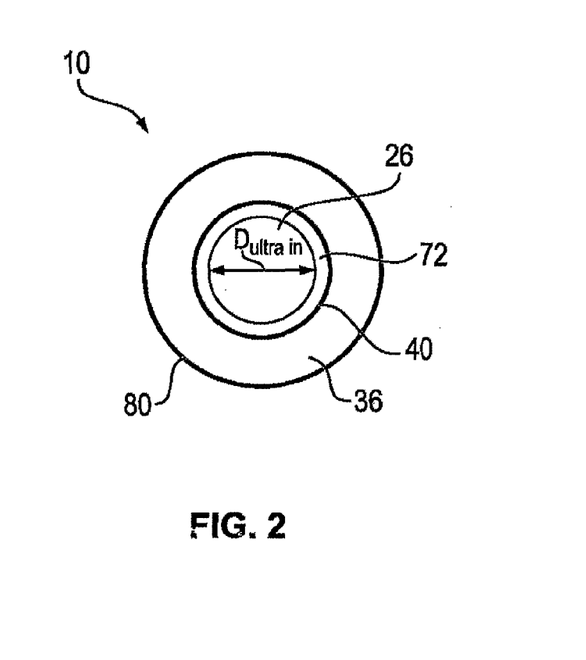
FIG. 2: a schematic plan view of the blood entry side.
Figure 3:
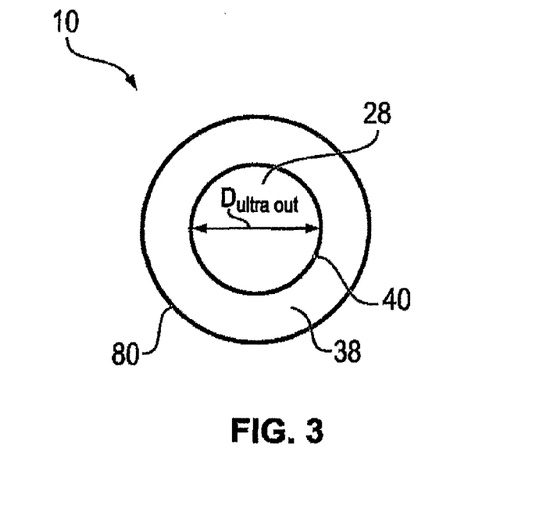
FIG. 3: a schematic plan view of the blood outlet side.

The fiber bundle 24 is sealed before closure, e.g. using a laser or hot stamp, on both end faces so that the ultrafilter membrane 22 of the first filter stage receive unilaterally closed fibers after the closing, that is in the end region 28, whereas the end region 26 is unclosed. In order reliably to preclude a direct overflow of dialysate through individual fibers into the dialysate space or blood space, the entry diameter for the dialysate is somewhat smaller due to a sealing ring 70 than the outlet diameter (cf. FIGS. 2 and 3). The sealing ring 70 lies on the ultrafilter fibers on the contact surface 72 and closes them.

The fiber module 10 is provided on the entry side with the especially designed end cap 50 in which the dialysate is supplied centrally via the connection 54 and the blood is supplied radially via the connection 52. The dialysate outlet 82 is here located radially at the housing 80. The arrows designate the flow direction D of the dialysate and the flow direction of the blood B.

The module is provided with a standard cap 60 having a central blood outlet 62 on the blood outlet side. It is generally also conceivable that the blood outlet is radially arranged.

Since the dialysate is discharged in the core of the fiber bundle 24, a good dialysate distribution is possible without diameter enlargement of the housing at the ends. A simple tube is therefore conceivable as a housing which is either integrated into a cassette or was extruded in an inexpensive manner.

The filter module 10 should be operated while lying horizontally to ensure good venting on priming. The dialysate outlet 82 and the (radial) blood outlet should face upwardly.

Alternatively, the module can be set slightly obliquely, with the blood inlet side being somewhat higher. In this case, it is meaningful to provide the inner tube or the boundary means 40 which separates the ultrafilter 20, that is the first filter stage, from the blood filter 30, that is the second filter stage 30, with a small venting opening 42 at the inlet side of the dialysate. A small amount of dialysate will here flow directly to the outlet during operation and the performance is negatively influenced. The opening should therefore preferably be kept very small.

The hollow fiber membranes 32 of the second filter stage 30 form a substantially hollow cylindrical fiber bundle 34 in which the bundle 24 is arranged. Both ends 36, 38 of the fiber bundle 34 are unclosed.

The fibers 32 for the blood purification can have an alignment which is not parallel to the axis X of the filter module 10. The fibers 32 then run at the periphery at an angle to the longitudinal axis about the core module (ultrafilter) and thus have a larger effective length. The ideal design of an ultrafilter (a plurality of short fibers) would hereby be combined with that of a blood filter requiring diffusion (longer bundles). This oblique laying of the blood filter fibers can run in the opposite direction, similar to the technique of yarn bobbins.

Figure 4:
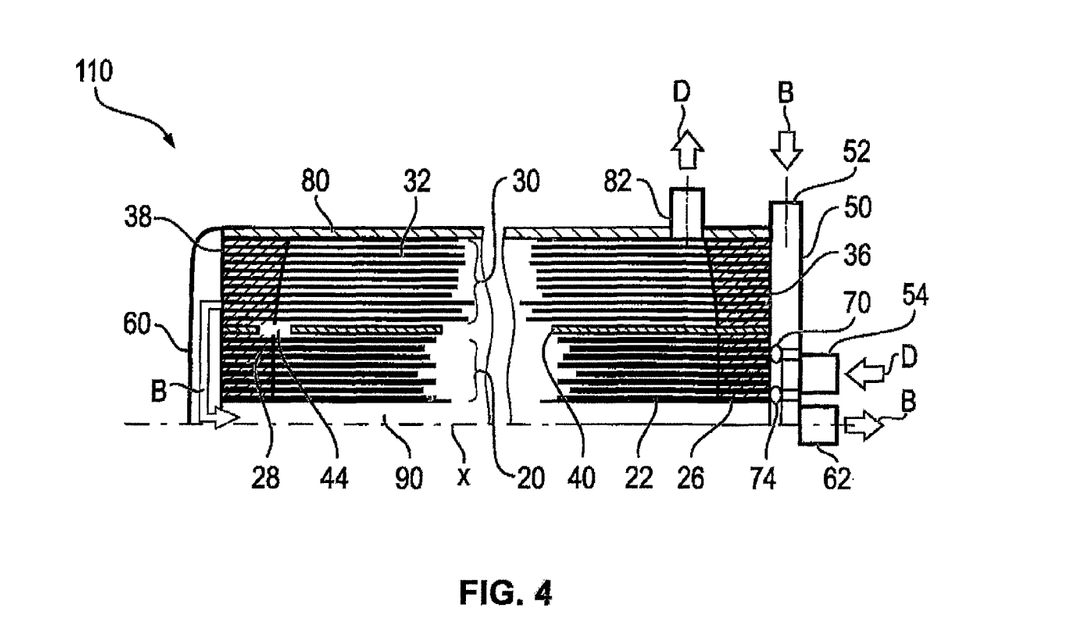
FIG. 4: a further schematic representation of a filter module in a second embodiment through a section along the central axis of symmetry of the concentric fiber bundle.

FIG. 4 shows a modified second embodiment of a filter module 110, with identical or comparable features being provided with identical reference numerals. The second embodiment substantially corresponds to the embodiment shown in FIG. 1 with the exception of the following differences.

Alternatively, the blood can also be returned to the cap 50 on the inlet side by a suitable cap 60 through a central tube 90 which could also be arranged horizontally on the periphery of the housing 80. The advantage of such a configuration is that all connections 52, 54, 62 and 82 are on one side of the module 110.

The cap 50 having the feed for blood and dialysate receives an additional sealing ring 74 to separate the blood outlet from the dialysate space.

Figure 5:
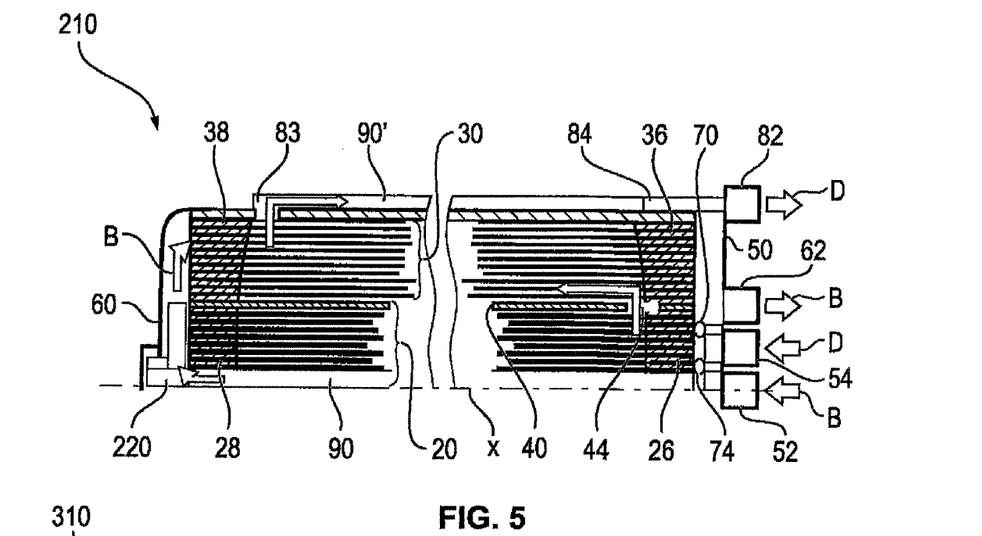
FIG. 5: a further schematic representation of a filter module in a third embodiment through a section along the central axis of symmetry of the concentric fiber bundle.

FIG. 5 shows a modified third embodiment of a filter module 210, with identical or comparable features being provided with identical reference numerals. The third embodiment also substantially corresponds to the embodiment shown in FIGS. 1 and 2 with the exception of the following differences. The blood inflow into the second filter stage 30 takes place via the passage 90 and via a deflection of blood flow B in the cap 60.

The rotor of an (impeller) pump 220 can additionally be integrated in the cap 60 and the flow in the filter module 210 can be reversed as a possible modification, but one which is not necessary. To achieve the flow reversal, the opening slits 44 for the internal dialysate outlet are displaced in the direction of the dialysate inlet 54 and the internal dialysate outlet 83 is moved in the direction of the pump cap 60.

To have all connections on one side, in this variant, the dialysate is returned in a passage 90' on the periphery of the housing 80. This channel 90' opens into the connection cap 50 in the connection 82 or in the dialysate outlet 82.

To facilitate the venting of the dialysate space, a small bore 84 can be provided just before the connection point to the end cap between the outwardly disposed dialysate passage 90' and the inner dialysate space. The bore 84 has to be kept small to minimize the bypass current of dialysate resulting therefrom.

Figure 6:
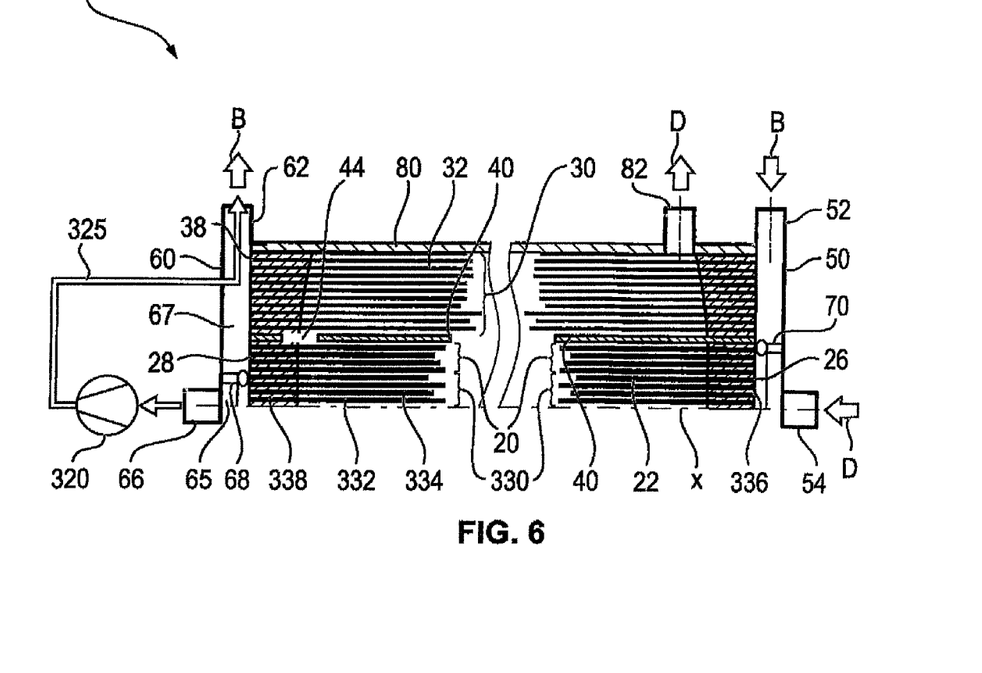
FIG. 6 a further schematic representation of a filter module in a fourth embodiment through a section along the central axis of symmetry of the concentric fiber bundle.

FIG. 6 shows a modified third embodiment of a filter module 310, with identical or comparable features being provided with identical reference numerals. The general setup is identical to the embodiment shown in FIG. 1.

The core of the hollow fiber membrane bundle in this variant comprises 2 ultrafilters formed by the first filter stage 20 and the third filter stage 330 in that the innermost fibers 332 of the third filter stager 330 have in comparison to the fibers 22 surrounding them of the first filter stage 20 closed ends 336 on the one side and open ends 338 on the oppositely disposed side. The housing cap 60 on the blood outlet side has an additional chamber 65 in the central region through which the infusate can flow to the pump 320 and from there via the line 325 into the blood region 67. This chamber 65 is separated from the blood region 67 by a seal 68.

A part flow of the dialysate flows around the hollow fiber membranes 32 of the second filter stage 30 as in the embodiment shown in FIG. 1 and is discharged again via the connector 82 located at the periphery. A second part flow of filtered dialysate is drawn at the center of the filter module 310 through the wall of the membranes 22 onto the lumen side of the third filter stage. An external pump (or a pump integrated in the cap similar to the pump 220 in accordance with the embodiment shown in FIG. 5) establishes the required pressure difference. The pump 320 establishes the underpressure in the bundle 334, that is in the third filter stage 330, since these fibers 332 have open ends 338 on the outlet side.

Figure 7:
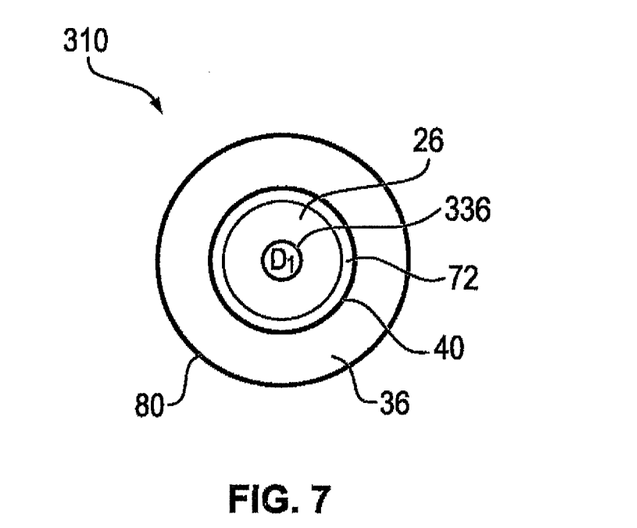
FIG. 7: a schematic plan view of the blood entry side.
Figure 8:
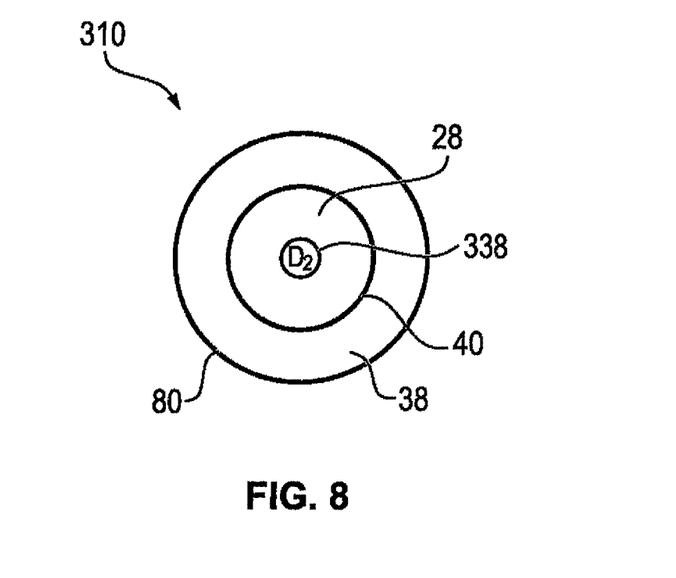
FIG. 8: a schematic plan view of the blood outlet side.

The outlet diameter D2 of this fiber bundle is smaller (cf. FIGS. 7 and 8) than the core diameter of the molded bundle on the inlet side D1. It is thus ensured that dialysate is always filtered in two stages before it e.g. is infused as postdilution and/or predilution. The outlet diameter D2 of the third filter stage 330 is thus designed smaller than the core diameter D1 of the third filter stage 330 in the inlet region. It is thereby achieved that individual fibers which are unexpectedly obliquely disposed in the total bundle by the production do not project from the third filter stage 330 into the first filter stage 20. A two-stage filtration is thereby advantageously ensured.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A disposable hemodialysis filter module comprising:
    a housing; and
    at least a first filter stage and a second filter stage which are substantially concentrically arranged inside said housing with the first filter stage surrounded by the second filter stage, said first filter stage and said second filter stage each including a plurality of hollow fiber membranes having a first fiber end and a second fiber end which are embedded in a respective casting compound,
    the first filter stage being a filter stage for a filtration of a first medical fluid and the second filter stage being a filter stage for the filtration of a second medical fluid, the first medical fluid being at least one of a dialyzing fluid and a substitution fluid, and the second medical fluid being blood,
    the first filter stage having unilaterally closed fiber ends, and the second filter stage having open fiber ends, and
    a boundary element which surrounds the first filter stage, which separates the first filter stage and the second filter stage from one another, and which has at least one opening which establishes a fluid communication between the first filter stage and the second filter stage, the boundary element being or including at least one of a film and a tube, and the opening in the boundary element being configured as one opening or as a plurality of openings arranged peripherally at the boundary element, with the hollow fiber membranes of the second filter stage having an alignment which is non-parallel to a longitudinal axis of the filter module, the first fiber ends of the first and second filter stage being embedded in a first casting compound common to the first and second stage, and the second fiber ends of the first and second filter stage being embedded in a second casting compound common to the first and second stage, with the first casting compound being separate from the second casting compound and the first and second casting compound arranged on opposite sides of the housing, and with the hollow fiber membranes of the second filter stage having a larger effective length than the hollow fiber membranes of the first filter stage due to the non-parallel alignment thereof.

2. The filter module in accordance with claim 1, wherein the boundary element has and/or forms a boundary wall, the opening in the boundary element in the boundary wall is arranged in a region adjacent to the casting compound, and/or the boundary element has at least one venting opening.

3. The filter module in accordance with claim 1, further comprising a first end cap in which a connection to the first filter stage and a connection to the second filter stage is arranged, with the fiber ends of the first filter stage being unclosed on the side of the first end cap and with at least one sealing element via which the unclosed fiber ends of the first filter stage can be sealed from the connection to the second filter stage and from the second filter stage.

4. The filter module in accordance with claim 3, wherein the filter module has a second end cap in which a connection to the second filter stage is arranged.

5. The filter module in accordance with claim 1, further comprising a housing in which the filter stages are arranged, with at least one connection to the first filter stage being arranged in the housing.

6. The filter module in accordance with claim 1, further comprising a passage element arranged concentrically and coaxially to at least one of the longitudinal axis of the filter module and the filter stages and being connected to the second filter stage, the passage element being provided on an outer side of the filter module.

7. The filter module in accordance with claim 1, further comprising a pump element or wherein the filter module is configured for connection to a pump element, the pump element pumping at least one of the first medical fluid and the second medical fluid.

8. The filter module in accordance with claim 7, wherein the pump element is at least one of a pump element integrated into the filter module and an impeller pump.

9. The filter module in accordance with claim 1, further comprising a third filter stage, with the first and the third filter stages being arranged with respect to one another such that the first medical fluid is introduced from the first filter stage via the hollow fiber membranes of the first and the third filter stages into the third filter stage.

10. The filter module in accordance with claim 9, wherein the first, the second and the third filter stages are arranged concentrically and coaxially, with the first filter stage surrounding the third filter stage and the second filter stage surrounding the first filter stage.

11. The filter module in accordance with claim 9, further comprising a first end cap in which a connection to the first filter stage and a connection to the second filter stage is arranged, with the fiber ends of the first filter stage being closed on a side of the first end cap, a sealing element with which the unclosed fiber ends of the first filter stage are sealed from an inflow to the first filter stage and from the second filter stage, with the fiber ends of the third filter stage being closed on the side of the first end cap, and a second end cap in which a connection to the third filter stage is arranged, with the fiber ends of the third filter stage being unclosed on the side of the second end cap.

12. The filter module in accordance with claim 10, further comprising a pump element connectable to a connection to the third filter stage, with at least one of the pump element being an integrated pump element and the connection to the third filter stage being connectable to a connection to the second filter stage.

13. The filter module according to claim 1, wherein the openings are peripherally arranged slits, perforations, holes, or labyrinth slits.

14. The filter module according to claim 1, wherein the hollow fiber membranes of the second filter stage extend at a periphery thereof at an angle to the longitudinal axis of the filter module about the first filter stage.

15. The filter module according to claim 1, wherein the second filter stage has at least a first and second laying of fibers extending in opposite directions obliquely to the longitudinal direction of the filter.

16. A disposable hemodialysis filter module comprising:
a housing; and
at least a first filter stage and a second filter stage which are substantially concentrically arranged inside said housing with the first filter stage surrounded by the second filter stage, said first filter stage and said second filter stage each including a plurality of hollow fiber membranes having a first fiber end and a second fiber end which are embedded in a respective casting compound, the first filter stage being a filter stage for a filtration of a first medical fluid and the second filter stage being a filter stage for the filtration of a second medical fluid, the first medical fluid being at least one of a dialyzing fluid and a substitution fluid, and the second medical fluid being blood, the first filter stage having unilaterally closed fiber ends, and the second filter stage having open fiber ends, and a boundary element which surrounds the first filter stage, which separates the first filter stage and the second filter stage from one another, and which has at least one opening which establishes a fluid communication between the first filter stage and the second filter stage, the boundary element being or including at least one of a film and a tube, and the opening in the boundary element being configured as one opening or as a plurality of openings arranged peripherally at the boundary element, with first fiber ends of the first and second filter stage being embedded in a first casting compound common to the first and second stage, and second fiber ends of the first and second filter stage being embedded in a second casting compound common to the first and second stage, with the first casting compound being separate from the second casting compound and the first and second casting compound arranged on opposite sides of the housing, with the second casting compound having a first region arranged centrally in the casting compound and embedding the second fiber ends of the first filter stage, with the second fiber ends of the first filter stage being closed in the first region of the second casting compound to provide a unilateral closure of the first filter stage, and
with the second casting compound having a second region integral with and peripherally surrounding the first region, the second region embedding the second fiber ends of the second filter stage, with the second fiber ends of the second filter stage being open in the second region of the second casting compound to provide an open end of the second filter stage.

* * * * *